United States Patent [19]

Terauchi et al.

[11] Patent Number: 5,532,421
[45] Date of Patent: Jul. 2, 1996

[54] METHOD FOR THE ISOMERIZATION OF CIS-ALKENYL COMPOUNDS

[75] Inventors: Takanobu Terauchi; Toyohisa Sakurada; Takehiko Fukumoto; Hiroshi Suzuki, all of Jyoetsu, Japan

[73] Assignee: Shin-Etsu Chemical Co., Ltd., Tokyo, Japan

[21] Appl. No.: 275,753

[22] Filed: Jul. 19, 1994

[30] Foreign Application Priority Data

Jul. 21, 1993 [JP] Japan ................... 5-179528

[51] Int. Cl.[6] .................................... C07C 5/27
[52] U.S. Cl. ............... 585/671; 554/125; 560/205; 562/598; 568/909.5; 570/256
[58] Field of Search ............ 585/671; 554/125; 560/205; 562/598; 568/909.5; 570/256

[56] References Cited

U.S. PATENT DOCUMENTS

| | | | |
|---|---|---|---|
| 2,310,225 | 2/1943 | Eipper | 554/125 |
| 4,814,460 | 3/1989 | Ikeda et al. | 548/262 |

FOREIGN PATENT DOCUMENTS

| | | |
|---|---|---|
| 502390 | 3/1939 | European Pat. Off. . |
| 55-167236 | 12/1980 | Japan . |
| 55-167237 | 12/1980 | Japan . |

OTHER PUBLICATIONS

Chemical Abstracts, vol. 86, No. 23, Jun. 6, 1977, Ichkawa et al, "Transcitral from cis-citral", p. 577.
Chemical Abstracts, vol. 72, No. 10, Mar. 9, 1970, Muromtseva et al, "Infrared spectroscopic study of processes occuring in rubbers . . . ", p. 58.
Chemical Abstracts, vol. 99, No. 15, Oct. 10, 1983, Zhou et al, "Use of nitric acid-sodium preparation of insect pheromones . . . ", p. 594.
Praxis Der Naturwissenschaften, Chemie, vol. 1981, No. 2, Feb. 15, 1981, pp. 61–62, Wolf, "Trans–isomerisierung der cis . . . ".

*Primary Examiner*—Ponnathapura Achutamurthy
*Attorney, Agent, or Firm*—Jacobson, Price, Holman & Stern

[57] ABSTRACT

An object of the present invention is to provide a method for the preparation of geometrical isomers which are important as constituents of synthetic pheromones, synthetic perfumes, terpenes and the like (i.e., a method for the isomerization of cis-alkenyl compounds to their trans-isomers). In this method, the above-described object is accomplished by reacting a cis-alkenyl compound in the presence of nitric acid used as the sole catalyst.

5 Claims, No Drawings

METHOD FOR THE ISOMERIZATION OF CIS-ALKENYL COMPOUNDS

FIELD OF THE INVENTION AND RELATED ART STATEMENT

This invention relates to a method for the preparation of geometrical isomers which are important as constituents of synthetic pheromones, synthetic perfumes, terpenes and the like. More particularly, it relates to a method for the isomerization of cis-alkenyl compounds to their trans-isomers.

In recent years, the technique of utilizing synthetic sex pheromones to predict the breeding of harmful insects or disturb communications between harmful insects has made great progress for the main purpose of controlling harmful insects of the order Lepidoptera. Thus, the utilization of synthetic sex pheromones is now in the stage of practical application.

Sex pheromones produced by lepidoptera are composed chiefly of unsaturated aliphatic compounds, and most of them are alkenes and alkadienyl compounds. Moreover, the position of an unsaturated bond or bonds in these components, their geometrical structure (i.e., cis- or trans-form), and the mixing ratio of these components have already been determined. The results thus obtained constitute an important factor to be considered in the synthesis of sex pheromones.

Conventionally known techniques for the isomerization of cis-isomers to trans-isomers are as follows:

An isomerization reaction using a mercapto-containing compound or a disulfide as a catalyst is described in Japanese Patent Publication Nos. 57608/'87 and 58337/'87.

Moreover, an isomerization reaction using elemental selenium (Se) as a catalyst is described in Journal of Am. Oil Chem. Soc., 26, 83, 1949.

Furthermore, an isomerization reaction using a mineral acid (e.g., nitrous acid, sulfurous acid or the like) as a catalyst and conducted in an organic solvent is described in Journal of Am. Oil Chem. Soc., 26, 83, 1949.

In addition, an isomerization method using nitrous acid derived from sodium nitrite and a mineral acid as a catalyst is described in the Journal of the Japanese Society of Chemical Synthesis, 38(7), 643–646, 1987.

However, these conventional techniques have the following respective disadvantages.

In the isomerization reaction using a mercapto-containing compound or a disulfide as a catalyst, the mercapto-containing compound used as a catalyst imparts an unpleasant mercapto odor to the products. This is especially undesirable in the case of perfume products having fragrance for their commercial value.

In the isomerization reaction using elemental selenium (Se) as a catalyst, selenium (Se) falls under the class of poisons as provided for according to the Poisonous and Deleterious Substances Control Law in Japan and is undesirable from the viewpoint of safety, hygiene and environmental protection.

The isomerization reaction using a mineral acid (e.g., nitrous acid, sulfurous acid or the like) as a catalyst and conducted in an organic solvent is undesirable in that it involves a high cost and requires a complicated procedure owing to the necessity of recovering the organic solvent. Moreover, mineral acids exhibit a powerful isomerizing activity, but have the disadvantage that they tend to cause polymerization and/or a shift of the double bond in olefinic compounds, resulting in a reduction in yield and purity. In particular, a shift of the double bond may cause a subtle change of odor in perfumes, and may produce impurities exerting a serious influence on biological activities in sex pheromones. Accordingly, it is very important to minimize the shifts of the double bonds.

The isomerization reaction using nitrous acid derived from sodium nitrite and a mineral acid as a catalyst is also undesirable in that it involves a high cost and the use of a mineral acid produces the same disadvantage as described above.

Thus, conventional isomerization techniques have their respective disadvantages and there has been a demand for the development of a new technique.

In view of these circumstances, it is an object of the present invention to provide a method for the isomerization of cis-alkenyl compounds to their trans-isomers with a high degree of isomerization and a high selectivity.

SUMMARY OF THE INVENTION

The present inventors made an intensive investigation for the purpose of solving the above-described problem. As a result, it has unexpectedly been found that, by adding 0.5 to 3% by weight of nitric acid (as expressed in terms of pure $HNO_3$) to cis-alkenyl compounds and reacting them at temperature of 60° to 150° C. for a period of 0.5 to 5 hours, their trans-isomers can be obtained at a degree of isomerization of 50 to 81% and a selectivity of 99 to 100%. Although 61% nitric acid was used in the examples given below, 65%, 70% and 98% products are also commercially available. Any of these products may be used in the present invention without difficulty.

As used herein, the term "degree of isomerization" means the percentage of the trans-isomer in the reaction product (i.e., the resulting mixture of cis- and trans-isomers). The term "selectivity" means the ratio of the purity of the reaction product (i.e., the resulting mixture of cis- and trans-isomers) to that of the starting material, and indicates the degree of reduction in purity due to side reactions such as a shift of the double bond during isomerization reaction.

As described above, the use of nitric acid as the sole catalyst makes it possible to isomerize cis-alkenyl compounds to their trans-isomers with a high degree of isomerization and a high selectivity. Moreover, this can overcome the disadvantages possessed by conventional techniques, such as safety problems and high cost.

DETAILED DESCRIPTION OF PREFERRED EMBODIMENTS

Several isomerization methods were compared with respect to cis-3-heptenol. The results thus obtained are summarized in Table 1 below.

TABLE 1

| Isomerization method (catalyst and other factor) | 2-Mercaptoethanol | Selenium (Se) | HCl + isopropanol | NaNO$_2$ + HCl | Nitric acid (as pure HNO$_3$) |
|---|---|---|---|---|---|
| Reaction conditions | Starting material, 300 g (2.6 moles) | Same as left | Same as left | Same as left | Same as left |
| | 2-Mercaptoethanol, 9 g | Se, 3 g | HCl, 15 g Isopropanol, 600 g | NaNO$_2$, 9 g Aqueous HCl, 24 g | HNO$_3$, 2 g |
| | Stirred at 90–100° C. for 4 hours | Stirred at 170–180° C. for 3 hours | Stirred at 80–90° C. for 3 hours | Stirred at 80–90° C. for 3 hours | Stirred at 80–90° C. for 3 hours |
| Degree of isomerization (%) | 58 | 62 | 52 | 66 | 77 |
| Selectivity (%) | 93 | 94 | 90 | 94 | 99 |

It can be seen from Table 1 that the isomerization method using nitric acid as a catalyst in accordance with the present invention is superior to the other methods in degree of isomerization and selectivity.

When nitric acid is used as the sole catalyst, the amount of catalyst added is generally in the range of 0.5 to 3% by weight (as expressed in terms of pure HNO$_3$), though it depends on the isomerizing tendency of the cis-alkenyl compound. For cis-alkenyl compounds having a relatively low molecular weight, it will suffice to add nitric acid in an amount of 0.5 to 1.5% by weight (as expressed in terms of pure HNO$_3$) based on the weight the cis-alkenyl compound. In some cases, the reaction may be conducted in the presence of toluene, xylene, n-hexane or the like.

The isomerization reaction is generally conducted at a temperature in the range of 80° to 100° C., though it depends on the structure of the cis-alkenyl compound. If the temperature is lower than 60° C., the degree of isomerization will be reduced to 5–10%, while if the temperature is unduly high, the selectivity will tend to lower.

Specific examples of cis-alkenyl compounds to which the method of the present invention can be applied include alkenes such as cis-3-hexene, cis-3-heptene and cis-3-decene; alkenols such as cis-3-hexenol, cis-3-heptenol, cis-3-octenol and cis-6-nonenol; alkenyl esters such as methyl oleate, cis-8-dodecenyl acetate and cis-3-hexenyl acetate; alkenyl halides such as cis-3-hexenyl chloride, cis-3-heptenyl chloride, cis-3-octenyl chloride and cis-3-decenyl chloride; and alkenoic acids such as oleic acid and cis-5-tetradecenoic acid. However, it is to be understood that the present invention is not limited thereto.

EXAMPLE 1

(Isomerization of cis-4-tridecenyl chloride with the aid of nitric acid)

500 g (2.3 moles) of cis-4-tridecenyl chloride and 7.5 g of nitric acid (as expressed in terms of pure HNO$_3$) were placed in a 2-liter reactor and stirred at 80°–85° C. for 3 hours. Thereafter, the mixture was washed with 500 g of a 5% aqueous solution of sodium hydroxide and then twice with 500-g portions of purified water.

The resulting substance was distilled to obtain 495 g of an oily liquid (with a vapor pressure of 2–3 mmHg at 130° C.).

Then, this product was examined for degree of isomerization and selectivity by gas chromatography.

Thus, a mixture of trans-4-tridecenyl chloride and cis-4-tridecenyl chloride was obtained at a degree of isomerization of 78% and a selectivity of 99%.

EXAMPLES 2–6

Attempts were made to isomerize other cis-alkenyl compounds in the same manner as in Example 1. The starting materials and reaction conditions employed are shown in Tables 2 and 3 below. Comparative Example 1
(Isomerization of cis-4-tridecenyl chloride with the aid of 2-mercaptoethanol)

500 g (2.3 moles) of cis-4-tridecenyl chloride, which was used for reaction in Example 1, was placed in a 2-liter reactor, and 25 g (0.32 mole) of 2-mercaptoethanol was added thereto. This mixture was stirred at 90°–95° C. for 3 hours. Then, the isomerization reaction was stopped by cooling the mixture to room temperature. Thereafter, the mixture was subjected to after-treatments as described in Example 1.

Thus, a mixture of trans-4-tridecenyl chloride and cis-4-tridecenyl chloride was obtained at a degree of isomerization of 62% and a selectivity of 93%.

Comparative Example 2

(Isomerization of cis-8-dodecenyl acetate with the aid of NaNO$_2$ and HCl)

500 g (2.2 moles) of cis-8-dodecenyl acetate, 15 g of NANO$_2$, and 40 g of a 20% aqueous solution of HCl were placed in a 2-liter reactor and stirred at 80°–90° C. for 3 hours. Then, the isomerization reaction was stopped by cooling the mixture to room temperature. Thereafter, the mixture was subjected to after-treatments as described in Example 1.

Thus, a mixture of trans-8-dodecenyl acetate and cis-8-dodecenyl acetate was obtained at a degree of isomerization of 65% and a selectivity of 93%.

The above-described results are summarized in Tables 2 and 3 below.

TABLE 2

|  | Example 1 | Example 2 | Example 3 | Example 4 |
|---|---|---|---|---|
| cis-Alkenyl compound | cis-4-Tridecenyl chloride | cis-3-Hexene | cis-3-Heptenol | cis-3-Octenyl chloride |
| Weight percentage of nitric acid (as pure HNO₃) based on starting material | 1.5 | 1.0 | 1.0 | 1.0 |
| Reaction temperature (°C.) | 80–85 | 60–65 | 80–85 | 85–90 |
| Reaction time (hrs) | 3.0 | 3.0 | 3.0 | 3.0 |
| Degree of isomerization (%) | 78 | 70 | 74 | 81 |
| Selectivity (%) | 99 | 100 | 99 | 99 |

TABLE 3

|  | Example 5 | Example 6 | Comparative Example 1 | Comparative Example 2 |
|---|---|---|---|---|
| cis-Alkenyl compound | Oleic acid | cis-8-Dodecenyl acetate | cis-4-Tridecenyl chloride | cis-8-Dodecenyl acetate |
| Weight percentage of nitric acid (as pure HNO₃) based on starting material | 1.5 | 1.5 | — | — |
| Reaction temperature (°C.) | 85–90 | 90–95 | 90–95 | 80–90 |
| Reaction time (hrs) | 3.0 | 3.0 | 3.0 | 3.0 |
| Degree of isomerization (%) | 78 | 80 | 62 | 65 |
| Selectivity (%) | 99 | 99 | 93 | 93 |

Application Example 1

(Synthesis of trans-4-tridecenyl acetate)

495 g (2.2 moles) of the mixture of trans-4-tridecenyl chloride and cis-4-tridecenyl chloride synthesized in Example 1, 432 g (4.4 moles) of potassium acetate, and 264 g (4.4 moles) of acetic acid were mixed under an atmosphere of nitrogen ($N_2$) and stirred at 180°–185° C. for 10 hours. Thereafter, this mixture was washed with 600 g of purified water and then with 600 g of a 5% aqueous solution of sodium bicarbonate. The resulting organic layer was purified by distillation. Thus, there was obtained 548 g (2.2 mole) of 4-tridecenyl acetate having a trans to cis ratio of 78:22 and a purity of 98%. This product is a sex pheromone component of the tomato pinworm (*Keiferia lycopersicella*) known as an insect pest of tomato fields principally in the United States of America.

We claim:

1. A method for the isomerization of a cis-alkenyl compound to their trans-isomers which comprises: a) reacting, under isomerization conditions the cis-alkenyl compound selected from the group consisting of alkenes, alkenols, alkenyl halides, alkenoic acids and alkenyl esters in the presence of a catalyst consisting essentially of nitric acid-has been inserted; and b) recovering the trans-isomer compound.

2. The method as claimed in claim 1 wherein the amount of the nitric acid is 0.5–3% by weight as expressed in terms of pure nitric acid based on the weight of the cis-alkenyl compound.

3. The method as claimed in claim 1 wherein the cis-alkenyl compound is 4-tridecenyl acetate.

4. The method as claimed in claim 1 wherein the isomerization reaction is conducted at a temperature in the range of 60° to 150° C.

5. The method as claimed in claim 4 wherein the isomerization reaction is conducted at a temperature in the range of 80° to 100° C.

* * * * *